United States Patent [19]

McGarry et al.

[11] 4,251,546

[45] Feb. 17, 1981

[54] PROCESS FOR KILLING INTERNAL HELMINTHS USING CERTAIN 1,1-BIS-(2-SUBSTITUTED-3-NITROPHENYL)ALKANE OR ALKYLENE DERIVATIVES

[75] Inventors: Errol-James McGarry, Bundoora; Bruce A. Forsyth, Croydon; Colin Wilshire, East Doncaster, all of Australia

[73] Assignee: ICI Australia Limited, Melbourne, Australia

[21] Appl. No.: 955,605

[22] Filed: Oct. 30, 1978

[30] Foreign Application Priority Data

Nov. 8, 1977 [AU] Australia ............................ PD2341

[51] Int. Cl.³ .................. A61K 31/055; A61K 31/10; A61K 31/22; A61K 31/08
[52] U.S. Cl. .................................... 424/347; 424/304; 424/305; 424/311; 424/331; 424/337; 424/340; 424/342
[58] Field of Search ............... 424/347, 348, 244, 267, 424/274, 342, 337, 340, 304, 331, 311, 305

[56] References Cited

U.S. PATENT DOCUMENTS

| | | | |
|---|---|---|---|
| 2,544,826 | 3/1951 | Craige | 424/347 |
| 2,615,052 | 10/1952 | Faith | 424/347 |
| 2,739,941 | 3/1956 | Chiddix et al. | 252/107 |
| 3,884,906 | 5/1975 | Van der Meer et al. | 424/348 |

FOREIGN PATENT DOCUMENTS

1034411 12/1958 Fed. Rep. of Germany.

OTHER PUBLICATIONS

*J.A.C.S.*, vol. 72, (1950), 837–839.
*Chemical Abstracts*, vol. 78, 1973, 58021j.
Chem. Abst., vol. 56 (1962) pp. 4661c to 4663d.

*Primary Examiner*—Frederick E. Waddell
*Attorney, Agent, or Firm*—Cushman, Darby & Cushman

[57] ABSTRACT

A method for killing internal parasites of warm blooded animals by treating the animals with an effective amount of a composition comprising a bis-(2-hydroxy-3-nitrophenyl)methane derivative; and novel bis(2-hydroxy-3-nitrophenyl)methane derivatives.

12 Claims, No Drawings

PROCESS FOR KILLING INTERNAL HELMINTHS USING CERTAIN 1,1-BIS-(2-SUBSTITUTED-3-NITROPHENYL)ALKANE OR ALKYLENE DERIVATIVES

This invention relates to a composition for killing internal parasites of warm blooded animals; in particular it relates to compositions for killing trematodes or nematodes. An example of a trematode is the liver fluke (*Fasciola hepatica*) which is a parasite of bile ducts of the liver of ruminants, such as cattle, sheep and goats. The liver fluke each year causes a significant amount of economic loss, not only from the death of the host animal but also from the deterioration in the value of meat and wool produced by infected animals. In cattle a loss in milk yield from liver fluke infection will also occur and in addition the loss sustained by the condemnation of infected livers as human food may also be considerable. An example of a nematode is *Haemonchus contortus* which is a nematode parasitic in the abomasum or fourth stomach of ruminants. It is a blood sucking parasite and when present in large numbers can cause anaemia and finally the death of the host. It can cause extensive losses, not only in the value of the animals which it may kill but also in the diminished production of commercial items such as wool and meat. There is therefore a commercial need to treat animals with chemicals which are both safe and effective in reducing the incidence and severity of diseases caused by both trematodes and nematodes.

We have now found a new class of compounds which are effective in killing trematodes and nematodes.

Accordingly we provide a process for killing internal parasites of warm blooded animals which process comprises treating the infected animal with an effective amount of a composition comprising as active ingredient a compound of the general formula I:

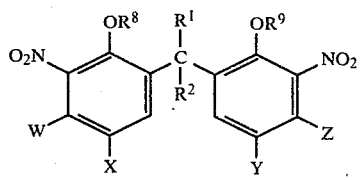

wherein $R^1$ and $R^2$ are independently chosen from hydrogen, optionally substituted lower alkyl, optionally substituted lower alkoxy, optionally substituted lower alkylthio, optionally substituted lower alkylsulphinyl, optionally substituted lower alkylsulphonyl, optionally substituted aryloxy, optionally substituted arylthio, optionally substituted arylsulphinyl, optionally substituted arylsulphonyl, halogen, hydroxy, cyano, nitro, thiocyano and the group $NR^3R^4$ wherein $R^3$ and $R^4$ are independently chosen from hydrogen, lower alkyl and aryl or $R^3$ and $R^4$ together with the nitrogen form a heterocyclic ring, or $R^1$ and $R^2$ together are =O, the group =$NR^5$ wherein $R^5$ is hydroxy, lower alkyl, aryl or arylamino, or the group =$CR^6R^7$ wherein $R^6$ and $R^7$ are independently chosen from hydrogen, lower alkyl, halogen, cyano, amino, nitro and carbamoyl; X and Y are independently chosen from halogen, nitro, cyano, optionally substituted lower alkyl, optionally substituted aryl, optionally substituted aryloxy, optionally substituted lower alkoxy, mercapto, optionally substituted lower alkylthio, optionally substituted lower alkylsulphinyl, optionally substituted lower alkylsulphonyl, sulpho, lower alkoxysulphonyl, thiocyano, amino, lower acylamino, lower alkylamino and di(lower alkyl)amino; W and Z are hydrogen or $OR^{10}$ and $OR^{11}$ respectively; and $R^8$, $R^9$, $R^{10}$ and $R^{11}$ are independently chosen from hydrogen, lower alkyl, lower acyl, lower alkenyl, carboxymethyl, lower (alkoxy) carbonylmethyl, aryloxyacetyl, lower (alkoxy) acetyl, lower alkoxy carbonyl and aroyl; or an optical isomer thereof; or a salt thereof; and a carrier therefor.

By lower alkyl and lower alkoxy we mean a group containing from 1 to 6 carbon atoms and by lower alkenyl and lower acyl we mean a group containing from 2 to 6 carbon atoms.

When, in the process of the invention, one or more of $R^1$, $R^2$, X and Y in the compound of general formula I is substituted lower alkyl, substituted lower alkoxy, substituted lower alkylthio, substituted lower alkylsulphinyl or substituted lower alkylsulphonyl, suitable substituents include, for example, one or more halogen atoms or hydroxy, lower alkoxy or optionally substituted aryl groups.

When, in the process of the invention, one or more of $R^1$, $R^2$, X and Y in the compound of general formula I is optionally substituted aryloxy, suitable aryloxy include, for example, phenyl optionally substituted with one or more atoms or groups chosen from halogen, lower alkyl, lower alkoxy, hydroxy, nitro and cyano.

When, in the process of the invention, one or more of X, Y or an optional substituent of a lower alkyl, lower alkoxy or lower alkylthio group in the compound of general formula I is optionally substituted aryl, suitable aryl include, for example, phenyl optionally substituted with one or more atoms or groups chosen from halogen, lower alkyl, lower alkoxy, hydroxy, nitro and cyano.

When one or both of $R^8$ and $R^9$ is hydrogen and/or one or both when one or both of $R^8$ and $R^9$ is hydrogen and/or one or both of W and Z is the group OH the compounds of general formula I may be used in the process of the invention in derivative form, conveniently as a salt of a pharmaceutically acceptable inorganic or organic base. Suitable bases include, for example, pharmaceutically acceptable alkali metal hydroxides, alkaline earth metal hydroxides and amines such as ammonia, triethanolamine and N-methylglutamine.

In a preferred aspect the invention provides a process as stated above wherein, in the compound of general formula I: $R^1$ and $R^2$ are independently chosen from hydrogen, the groups $C_1$ to $C_6$ alkyl, $C_1$ to $C_6$ alkoxy and $C_1$ to $C_6$ alkylthio wherein each group is optionally substituted with one or more substituents chosen from halogen, $C_1$ to $C_6$ alkoxy and phenyl optionally substituted with one or more substituents chosen from halogen, nitro, cyano and $C_1$ to $C_6$ alkoxy, and the groups aryloxy and arylthio wherein each aryl group is phenyl optionally substituted with one or more substituents chosen from halogen, nitro, cyano and $C_1$ to $C_6$ alkoxy, or $R^1$ and $R^2$ together form the group =$CR^6R^7$ wherein $R^6$ and $R^7$ are independently chosen from hydrogen and halogen;

X and Y are independently chosen from hydrogen and halogen; W and Z are hydrogen; and $R^8$ and $R^9$ are independently chosen from hydrogen, $C_1$ to $C_6$ alkanoyl; $C_1$ to $C_6$-(alkoxy)carbonyl and the cation of an inorganic or organic base.

In a more preferred aspect the invention provides a process as stated above wherein, in the compound of general formula I:

one of $R^1$ and $R^2$ is hydrogen and the other is chosen from the groups $C_1$ to $C_6$ alkyl and $C_1$ to $C_6$ alkoxy wherein each group is optionally substituted with one or more substituents chosen from halogen, $C_1$ to $C_6$ alkoxy and phenyl optionally substituted with one or more substituents chosen from halogen, nitro, cyano and $C_1$ to $C_6$ alkoxy, and the group phenoxy optionally substituted with one or more substituents chosen from halogen, nitro, cyano and $C_1$ to $C_6$ alkoxy, or $R^1$ and $R^2$ together form the group $=CCl_2$;

X and Y are independently chosen from halogen;
W and Z are hydrogen; and
$R^8$ and $R^9$ are independently chosen from hydrogen and the cation of an inorganic or organic base.

In an even more preferred aspect the invention provides a process as described above wherein, in the compound of general formula I:

either one of $R^1$ and $R^2$ is hydrogen and the other is a $C_1$ to $C_6$ haloalkyl group or $R^1$ and $R^2$ together form the group $=CCl_2$;

X and Y are independently chosen from halogen;
W and Z are hydrogen; and
$R^8$ and $R^9$ are independently chosen from hydrogen and the cation of an inorganic or organic base.

Compounds which may be used in the process of the invention include, but are by no means limited to, the following:

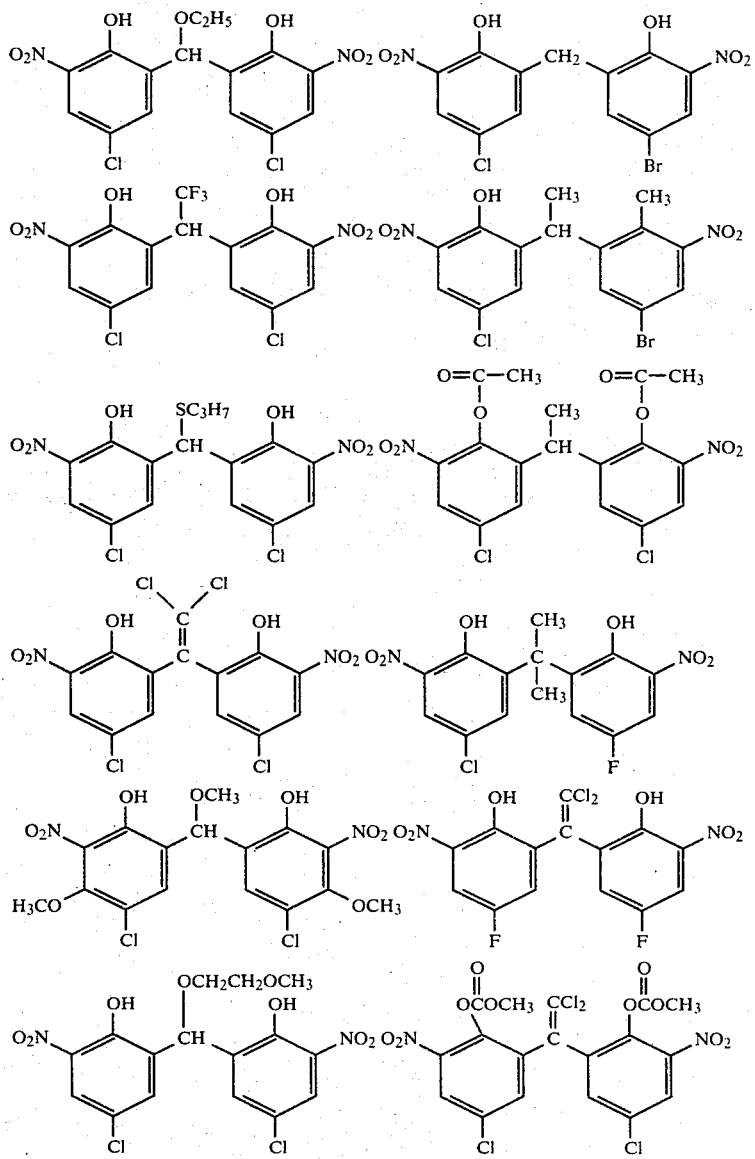

Many of the compounds useful in the process of the invention are new compounds. Thus in a further embodiment the invention provides novel compounds of general formula I wherein $R^1$, $R^2$, W, X, Y, Z, $R^8$ and $R^9$ may take any of the values hereinbefore defined and wherein if $R^1$ and $R^2$ are independently chosen from hydrogen and $C_1$ to $C_6$ alkyl or if one of $R^1$ and $R^2$ is hydrogen and the other is a $C_1$ to $C_6$ chloroalkyl group, then one of X and Y is a substituent other than chlorine, bromine or iodine.

The compounds which may be used in the process of the invention may be prepared by methods known to those skilled in the art. For example, the compounds of formula I as hereinbefore defined can be prepared either by:

(a) condensation of one mole of a 2-(1-hydroxyalkyl)-phenol or a phenolic derivative thereof with one mole of a para-substituted phenol or a phenolic derivative thereof followed by nitration with a suitable nitrating agent; or

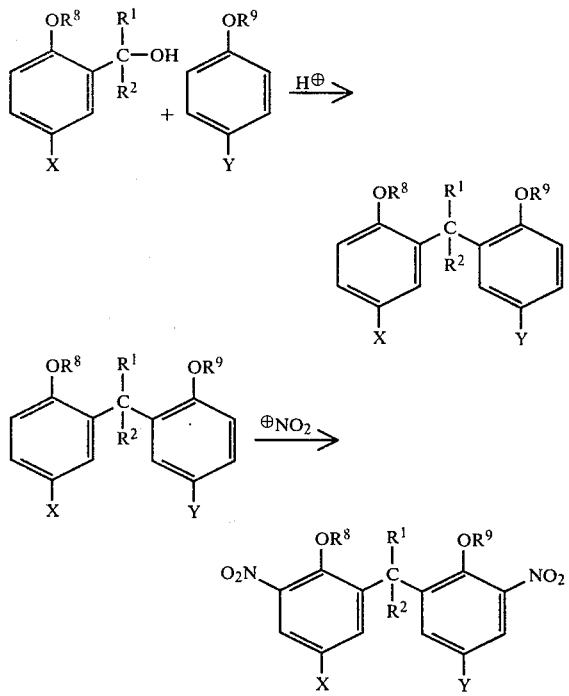

(b) condensation of two moles of a para-substituted phenol or a phenolic derivative thereof with one mole of a halo-substituted aliphatic aldehyde followed by nitration with a suitable nitrating agent; or

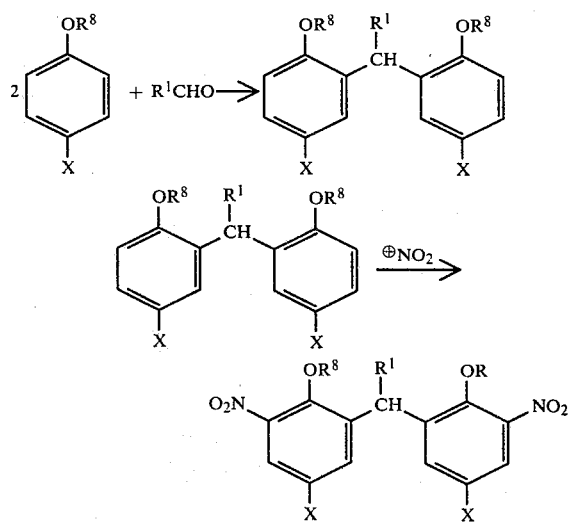

(c) reduction of a 2,2'-dihydroxy-3,3'-dinitrobenzophenone or a phenolic derivative thereof to the corresponding carbinol, reaction of the carbinol to replace the alcoholic hydroxyl with a good leaving group and reaction of the compound so formed with an oxygen or sulfur nucleophile to replace the leaving group with the nucleophilic group; or

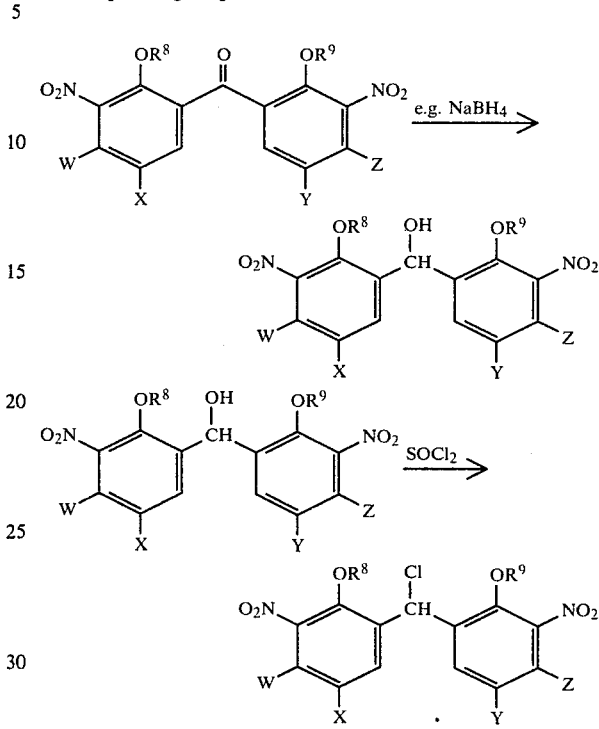

(d) reduction of a 5,5'-disubstituted 2,2'-dihydroxybenzophenone or phenolic derivative thereof to the corresponding carbinol, reaction of the carbinol to replace the alcoholic hydroxyl with a good leaving group, reaction of the compound so formed with an oxygen or sulfur nucleophile to replace the leaving group with the nucleophilic group, and nitration of the intermediate carbinol or derivative thereof to give a 2,2'-dihydroxy-3,3'-dintro-5,5'-disubstituted diphenylmethane or phenolic derivative thereof; or (e) the dehydrohalogenation of a compound of general formula I prepared as described according to (a), (b), (c) and (d) above wherein one of $R^1$ and $R^2$ is hydrogen and the other is an α-halo-substituted alkyl group.

The condensation reactions described in paragraphs (a) and (b) above are preferably carried out in the presence of an acid catalyst.

Compounds of general formula I wherein one or both of $R^8$ and $R^9$ are not hydrogen alternatively may be prepared from the corresponding phenols of general formula I by methods known to those skilled in the art for the preparation of phenolic derivatives.

In the method of the invention the compounds are preferably used in the form of a composition which comprises an inert carrier.

The compositions are of particular use for the treatment of Fasciola sp. including *Fasciola hepatica* and *Fasciola gigantica* and Haemonchus sp. including *Haemonchus contortus.*

For effective treatment, certain dosage levels are desired depending upon the compound employed, the type of animal to be treated and the particular helminth being combatted. In general, efficacy against fluke is achieved when the composition is administered in a single dose at dosage levels of from about 1 to 50 mg active ingredient/kg of animal body weight, and preferably from about 1 to 20 mg active ingredient per kg of animal body weight.

The compositions of the present invention may be administered in a variety of ways, depending upon the particular animal employed, the type of anthelmintic treatment normally given to such an animal, the materials employed, and the particular helminths being combatted. It is preferred to administer them in a single efficacious oral or parenteral dose at a time when fluke or nematode infection is apparent or suspected. They may be employed alone or in combination with other anthelmintics, parasiticides or antibacterials. The compounds may also be applied as a "pour on" formulation for dermal application. The amounts of the active anthelmintic ingredient in the composition, as well as the remaining constituents are varied according to the type of treatment to be employed, the host animal, and the particular parasitic disease being treated. In general, however, compositions containing a total weight percent of the active compound or compounds ranging from 0.001 to 95% will be suitable with the remainder being any suitable carrier or vehicle. Furthermore, the compositions should contain enough of the active ingredient to provide an effective dosage for the proper treatment of the parasitic disease.

A number of modes of treatment may be employed, and each to some extent determines the general nature of the composition. For example, the anthelmintic compositions may be administered to domesticated animals in single unit oral dosage form such as a tablet, bolus, capsule or drench; in a liquid form suitable for parenteral administration; or they may be compounded as feed premix to be later admixed with the animal's food.

When the compositions are to be solid unit dosage forms as in tablets, capsules, or boluses, the ingredients other than the active ingredient may be any other pharmaceutically acceptable vehicles convenient in the preparation of such forms, and preferably materials nutritionally suitable such as starch, lactose, talc, magnesium stearate, vegetable gums, and the like. Moreover when capsules are employed, the active compound may be used in essentially undiluted form, the only extraneous material being that of the capsule casing itself which may be hard or soft gelatin or any other pharmaceutically acceptable encapsulating material. When the dosage form is to be used for parenteral administration, the active material is suitably admixed with an acceptable base vehicle. In all of such forms, i.e. in tablets, boluses, capsules, and injectable formulations, the active compound conveniently ranges from about 5 to 80% by weight of the total composition.

When the unit dosage form is to be in the form of a drench, the active ingredient may be mixed with agents which will aid in the subsequent suspending of the active compound in water, such as bentonite, clays, water-soluble starch, cellulose derivatives, gums, surface active agents and the like to form a dry predrench composition, and this predrench composition added to water just before use. In the predrench formulation, in addition to the suspending agent, such ingredients as preservatives, antifoam compounds, and the like, may be employed. Such a dry product may contain as much as 95% by weight of the active compound, the rest being contributed by the excipients. Preferably, the solid composition contains from 30% to 95% by weight of the active compound. Enough water should be added to the solid product to provide the proper dosage level within a convenient amount of liquid for a single oral dose. Liquid drench formulations containing from about 10 to 50 weight percent of dry ingredients will in general be suitable with the preferred range being from 15 to 30 weight percent. Where the compositions are intended to be used as feeds, feed supplements, or feed premixes, they will be mixed with suitable ingredients of an animal's nutrient ration. The solid orally-ingestible carriers normally used for such purposes, such as distillers' dried grains, corn meal, citrus meal, fermentation residues, ground oyster shells, Attapulgus clay, wheat shorts, molasses solubles, corn cob meal, edible vegetable substances, toasted dehulled soya flour, soybean mill feed, antibiotics mycelia, soya grits, crushed limestone and the like are all suitable. The active compounds are intimately dispersed or admixed throughout the solid inert carrier by methods such as grinding, stirring, milling or tumbling. By selecting proper diluents and by altering the ratio of carrier to active ingredient, compositions of any desired concentration may be prepared. Feed supplement formulations containing from about 10 to 30% by weight of active ingredient are particularly suitable for addition of feeds. The active compound is normally dispersed or mixed uniformly in the diluent but in some instances may be adsorbed on the carrier.

These supplements are added to the finished animal feed in an amount adequate to give the final concentration of active ingredient desired for controlling or treating the helminth infection by way of the animal ration. Although the preferred level in feeds will depend on the particular compounds being employed, the active ingredients of this invention are normally fed at levels of 0.05–25% in the feed. As stated above, animals are preferably treated at a time when the infestation is apparent or suspected and the most preferred method for such treatment is via the single oral dose technique. Thus administration of medicated feed is not preferred but may certainly be employed. Similarly, the amounts of drug present in the feed may be reduced to levels in the order of 0.001% to 3.0 weight percent based on the weight of feed, and the medicated feed administered over prolonged periods. This would be in the nature of a preventive or propylactaic measure but again is not the mode of choice. Another method of administering the compositions of this invention to animals whose feeds are conveniently pelleted, such as sheep, is to incorporate them directly in the pellets. For instance, the compositions are readily incorporated in nutritionally adequate alfalfa pellets at levels of 2 to 110 grams per pound of pellets for therapeutic use, and at lower levels for example 80 to 1000 milligrams per pound for prophylactic use, and such pellets fed to the animals. The compositions may also optionally contain other drugs of veterinary utility. Veterinary drugs which may be present in the veterinary compositions of this invention, depending upon the mode of administration of the said compositions, include for example, piperazine, 1-diethyl-carbamyl-4-methyl-piperazine, tetrachlorethylene, organic and inorganic arsenical compounds, tetramisole, 2-phenyl-benzimidazole, thiabendazole, phenothiazine, mebendazole and pyrantel salts.

The compositions may be administered to the animal by parenteral dose and in a further aspect of our invention we provide an injectable composition comprising a sterile solution containing from 5 to 70% w/w preferably 5 to 50% w/w of the active ingredient in a pharmaceutically acceptable solvent.

The composition may be sterilized by methods known to those skilled in the art for the sterilization of injectable solution such as, for example, ultra filtration or gamma radiation.

The compositions may also be administered by application to the skin of the animal and in yet a further aspect the invention provides a liquid composition for external application to an animal said composition comprising a solution or suspension containing from 1 to 70% w/w preferably 1 to 10% w/w of the active ingredient in a pharmaceutically acceptable liquid carrier. Suitable liquid carriers include, for example, pharmaceutically acceptable hydrocarbons, ketones, esters, ethers, alcohols, amides, sulphones and sulphoxides.

The invention is now illustrated by, but by no means limited to, the following examples in which all parts are part by weight unless otherwise specified.

EXAMPLE 1

Preparation of
1-(5-Bromo-2-hydroxy-3-nitrophenyl)-1-(5-chloro-2-hydroxy-3-nitrophenyl)ethane (8)

Sodium borohydride (0.5 g) was added in small portions to a cooled solution of 5-chloro-2-hydroxyacetophenone (5 g) in methanol (50 ml). The solution was stirred at room temperature for 0.5 hr and was then poured into ice-water and acidified with dilute acetic acid. The product was extracted with ether, the ethereal solution was washed with water and then 5% aqueous sodium bicarbonate solution. The ethereal solution was dried ($Na_2SO_4$) and the solvent removed under reduced pressure. The colourless oil crystallised from hexane/ethyl acetate to give 4-chloro-2-(1-hydroxyethyl)-phenol (4.8 g); m.p. 98° C.

4-Chloro-2-(1-hydroxyethyl)phenol (4 g) was added slowly to a melt of 4-bromophenol (7.9 g) and concentrated hydrochloric acid (3 drops) at 100° C. The melt was heated at this temperature for 3 hr and then cooled and the product crystallised from benzene/hexane to give 1-(5-bromo-2-hydroxyphenyl)-1-(5-chloro-2-hydroxyphenyl)ethane (3.3 g); m.p. 167° C.

Concentrated nitric acid (2.0 ml) was added dropwise to a cooled solution of 1-(5-bromo-2-hydroxyphenyl)-1-(5-chloro-2-hydroxyphenyl)ethane (1.6 g) in glacial acetic acid (16 ml). The mixture was then stirred at room temperature for 30 min before pouring into ice water. The yellow solid was collected by filtration and crystallised from ethanol to give 1-(5-bromo-2-hydroxy-3-nitrophenyl)-1-(5-chloro-2-hydroxy-3-nitrophenyl)ethane (0.7 g); m.p. 161° C.

Compounds 1 to 7 inclusive, 9 and 10 listed in Table 1 (page 22) were prepared from the appropriate starting materials following the general method described above.

EXAMPLE 2

Preparation of
1,1-Bis(5-chloro-2-hydroxy-3-nitrophenyl)-2,2,2-trifluoroethane (53)

A mixture of 4-chlorophenol (51.2 g), trifluoroacetaldehyde methyl hemiacetal (26 g) and acetic acid (16 ml) was stirred at a temperature of 14° C. and concentrated sulfuric acid (60 ml) was added slowly and the temperature of the mixture was kept below 25° C. The mixture was then stirred for a period of 2 hours at a temperature of 40° C. and the mixture poured into water. The product was recrystallised from cyclohexane/diethyl ether to give 1,1-bis(5-chloro-2-hydroxyphenyl)-2,2,2-trifluoroethane (25 g), m.p. 144° C.

1,1-Bis(5-chloro-2-hydroxyphenyl)-2,2,2-trifluoroethane (25 g) was nitrated following the nitration procedure described in Example 1 to give 1,1-bis(5-chloro-2-hydroxy-3-nitrophenyl)-2,2,2-trifluoroethane (27 g), m.p. 135° C.

Compounds 11 to 18 inclusive and 54 to 56 inclusive listed in Table 1 were prepared from the appropriate starting materials following the general method described above. (Compounds 14 to 18 inclusive were prepared by the dehydrohalogenation of the corresponding compound of formula I wherein $R^1$ is trichloromethyl and $R^2$ is hydrogen).

TABLE I $$O_2N \underset{X}{\underset{\|}{\bigcirc}} \overset{OR^8}{\underset{R^2}{\overset{R^1}{\underset{|}{C}}}} \overset{OR^9}{\underset{Y}{\underset{\|}{\bigcirc}}} NO_2$$

| COMPOUND NO | $R^1$ | $R^2$ | X | Y | $R^8, R^9$ | PHYSICAL DATA m.p. °C. |
|---|---|---|---|---|---|---|
| 1 | H | H | Cl | Cl | H | 179 |
| 2 | H | H | F | F | H | 134 |
| 3 | H | H | Cl | Br | H | 178 |
| 4 | $CH_3$ | H | F | F | H | 126 |
| 5 | $CH_3$ | H | F | Cl | H | 129 |
| 6 | $CH_3$ | H | F | Br | H | 119 |
| 7 | $CH_3$ | H | Cl | Cl | H | 161–3 |
| 9 | $CH_3$ | H | Br | Br | H | 162 |
| 10 | $CH_3$ | H | Br | I | H | 131 |
| 11 | $CCl_3$ | H | Cl | Cl | H | 233 |
| 12 | $CCl_3$ | H | Br | Br | H | 211 |
| 13 | $CCl_3$ | H | F | F | H | 174 |
| 14 | $=CCl_2$ | | Cl | Cl | H | 166 |
| 15 | $=CCl_2$ | | Br | Br | H | 213 |
| 16 | $=CCl_2$ | | F | F | H | 108 |
| 17 | $=CCl_2$ | | Cl | Cl | $COCH_3$ | 195 |
| 18 | $=CCl_2$ | | Cl | Cl | $CO_2CH_3$ | 200 |
| 53 | $CF_3$ | H | Cl | Cl | H | 135 |
| 54 | $C_2F_5$ | H | Cl | Cl | H | 140 |
| 55 | $n-C_3F_7$ | H | Cl | Cl | H | 102 |
| 56 | $CF_3$ | H | Br | Br | H | 146 |

EXAMPLE 3

Preparation of 2,2'-Isopropylidene bis(4-fluoro-6-nitrophenol) (19)

Dimethyl sulphate (30 ml) was added dropwise over 45 min to a stirred mixture of 5-fluoro-2-hydroxyacetophenone (32.43 g) and potassium carbonate (40.5 g) in acetone (500 ml) and the mixture was then heated under reflux for 8 hr. Concentrated ammonia solution was added and the inorganic solids removed by filtration. The solvent was removed under reduced pressure and the product was dissolved in ether and washed with water. After drying the ethereal solution ($Na_2SO_4$) the ether was removed under reduced pressure and the residue was distilled to give 5-fluoro-2-methoxyacetophenone (28.4 g); b.p. 58°–64 ° C./0.2 mm.

5-fluoro-2-methoxyacetophenone (10 g) in dry ether (50 ml) was added dropwise over 20 min to a solution of methyl magnesium iodide [from magnesium (1.6 g) and methyl iodide (4.05 ml)] in ether (50 ml). The mixture was stirred at room temperature for 1.5 hr and then was heated under gentle reflux for 30 min. An ice cold solution of ammonium chloride was added and the ether layer was separated and dried (Na₂SO₄). After evaporation of the solvent 2-(5-fluoro-2-methoxyphenyl)propan-2-ol (9.1 g) crystallised from hexane; m.p. 69°–70° C.

2-(5-fluoro-2-methoxyphenyl)propan-2-ol (6 g) was added in small portions to a melt of 4-fluorophenol (12 g) and concentrated hydrochloric acid (10 days) at 90° C. The mixture was stirred at this temperature overnight and was then cooled and dissolved in ether. The excess of p-fluorophenol was removed by extraction with 5% aqueous sodium hydroxide solution. The alkali insoluble material crystallised from hexane to give 2-(5-fluoro-2-hydroxyphenyl)-2-(5-fluoro-2-methoxyphenyl)propane (3.9 g) as colourless prisms; m.p. 90° C.

Boron tribromide (1 ml) in dichloromethane (10 ml) was added dropwise to a solution of 2-(5-fluoro-2-hydroxyphenyl)-2-(5-fluoro-2-methoxyphenyl)propane (0.5 g) in dichloromethane (10 ml) at −70° C. The solution was stirred at this temperature for one hour and water was then added. The organic layer was separated, dried (Na₂SO₄) and the solvent removed to give a colourless product which crystallised from hexane to give colourless prisms of 2,2'-isopropylidene bis(4-fluorophenol) (0.375 g); m.p. 155° C.

Concentrated nitric acid (0.85 ml) was added dropwise to a solution of 2,2'-isopropylidene bis(4-fluorophenol) (1.1 g) in glacial acetic acid (10 ml). The solution was stirred at room temperature for 15 hr and then poured into ice water. The yellow solid was filtered and crystallised from ethanol to give yellow needles of 2,2'-isopropylidene bis(4-fluoro-6-nitrophenol) (1.0 g); m.p. 138° C.

EXAMPLE 4

Preparation of
2-(5-chloro-2-hydroxy-3-nitrophenyl)-2-(5-fluoro-2-hydroxy-3-nitrophenyl)propane (20)

2-(5-chloro-2-hydroxyphenyl)-2-(5-fluoro-2-methoxyphenyl)propane (m.p. 97° C.) was prepared from 2-(5-fluoro-2-methoxyphenyl)propan-2-ol and 4-chlorophenol following the method described in Example 3 for the preparation of 2-(5-fluoro-2-hydroxyphenyl)-2-(5-fluoro-2-methoxyphenyl)propane.

2-(5-chloro-2-hydroxyphenyl)-2-(5-fluoro-2-hydroxyphenyl)propane (m.p. 125° C.) was prepared from 2-(5-chloro-2-hydroxyphenyl)-2-(5-fluoro-2-methoxyphenyl)propane following the method described in Example 3 for the preparation of 2,2'-isopropylidene bis(4-fluorophenol).

2-(5-chloro-2-hydroxy-3-nitrophenyl)-2-(5-fluoro-2-hydroxy-3-nitrophenyl)propane (m.p. 160° C.) was prepared from 2-(5-chloro-2-hydroxyphenyl)-2-(5-fluoro-2-hydroxyphenyl)propane following the method described in Example 3 for the preparation of 2,2'-isopropylidene bis(4-fluoro-6-nitrophenol).

EXAMPLE 5

Preparation of 2,2'-Isopropylidene bis(4-chloro-6-nitrophenol) (21)

2-(5-chloro-2-methoxyphenyl)propan-2-ol (m.p. 56° C.) was prepared from 5-chloro-2-methoxyacetophenone following the method described in Example 3 for the preparation of 2-(5-fluoro-2-methoxyphenyl)propan-2-ol.

2-(5-chloro-2-hydroxyphenyl)-2-(5-chloro-2-methoxyphenyl) propane (m.p. 137° C.) was prepared from 2-(5-chloro-2-methoxyphenyl)propan-2-ol and 4-chlorophenol following the method described in Example 3 for the preparation of 2-(5-fluoro-2-hydroxyphenyl)-2-(5-fluoro-2-methoxyphenyl)propane.

2,2'-isopropylidene bis(4-chlorophenol) (m.p. 142° C.) was prepared from 2-(5-chloro-2-hydroxyphenyl)-2-(5-chloro-2-methoxyphenyl)propane following the method described in Example 3 for the preparation of 2,2'-isopropylidene bis(4-fluorophenol).

2,2'-isopropylidene bis(4-chloro-6-nitrophenol) (m.p. 188° C.) was prepared from 2,2'-isopropylidene bis(4-chlorophenol) following the method described in Example 3 for the preparation of 2,2'-isopropylidene bis(4-chloro-6-nitrophenol).

EXAMPLE 6

Preparation of
Bis(5-chloro-2-hydroxy-3-nitrophenyl)ketone (22)

Bis(5-chloro-2-methoxyphenyl)ketone (m.p. 108° C.) was prepared by the oxidation of 2,2'-methylenebis(5-chloroanisole) following the method described by Moshfegh et al (Acta Chem. Scand, 1957, 40, 1157–66) for the oxidation of 2,2'-methylenebis(5-chlorophenetole).

Bis(5-chloro-2-hydroxyphenyl)ketone (m.p. 154° C.; reference m.p. 152°–155° C.) was prepared by the demethylation of bis(5-chloro-2-methoxyphenyl)ketone following the method described by Moshfegh et al (Acta Chem Scand, 1957, 40, 1157–66) for the de-ethylation of bis(5-chloro-2-ethoxyphenyl)ketone.

Nitric acid (4 ml) was added dropwise to a stirred solution of bis(5-chloro-2-hydroxyphenyl)ketone (2.7 g) in glacial acetic acid (50 ml). The solution was stirred at room temperature for 1 hr and during this time a yellow solid separated from solution. The mixture was poured into ice water and the product collected by filtration. Thin layer chromatography indicated that the product was a mixture of two compounds which were separated by column chromatography on silica gel. Elution with hexane containing increasing amounts of ethyl acetate afforded 5-chloro-2-hydroxyphenyl 5-chloro-2-hydroxy-3-nitrophenyl ketone (150 mg) m.p. 153° C., followed by bis-(5-chloro-2-hydroxy-3-nitrophenyl)ketone (1.5 g), m.p. 187° C.

EXAMPLE 7

Preparation of
Bis(5-chloro-2-hydroxy-3-nitrophenyl)methyl chloride (23)

Sodium borohydride (3.5 g) was added portionwise to a stirred solution of bis(5-chloro-2-hydroxy-3-nitrophenyl) ketone (10 g) in ethanol (150 ml) the solution being maintained at a temperature of 0° C. On completion of the addition the temperature of the solution was allowed to rise to ambient temperature and the mixture was stirred overnight at ambient temperature. The solution was diluted with water, acidified with hydrochloric acid and the product extracted into ethyl acetate. The solvent was removed by distillation under reduced pressure to give bis-(5-chloro-2-hydroxy-3-nitrophenyl)methyl alcohol (9.0 g) which on recrystallisation from ethanol/hexane had a melting point of 180° C.

A mixture of bis(5-chloro-2-hydroxy-3-nitrophenyl)methyl alcohol (4.5 g) and thionyl chloride (50 ml) was heated under reflux for 3 hr. Dimethylformamide (0.1 g) was added to the reaction mixture and the mixture was heated under reflux for a further hour. Excess thionyl chloride was then removed by distillation under reduced pressure and the remaining red oil was crystallised from ethanol to give 4 g of bis(5-chloro-2-hydroxy-3-nitrophenyl)methyl chloride, m.p. 180° C.

EXAMPLE 8

Preparation of Bis(5-chloro-5-hydroxy-3-nitrophenyl)methyl isobutyl ether (24)

A mixture of bis(5-chloro-2-hydroxy-3-nitrophenyl)-methyl chloride (5 g) and isobutanol (50 ml) was stirred at a temperature of 0° C. and sodium hydride (1 g) was added portionwise. On completion of the addition the mixture was stirred for a further hour and poured into water. The aqueous solution was extracted into ether/petroleum ether and the solvents removed by distillation under reduced pressure. The residue was recrystallised from petroleum ether (b.p. 40°-60° C.) to give 4.3 g of bis(5-chloro-2-hydroxy-3-nitrophenyl)methyl isobutyl ether m.p. 95° C.

EXAMPLE 9

The compounds listed in Table 2 below were prepared from bis(5-chloro-2-hydroxy-3-nitrophenyl)-methyl chloride and the appropriate alcohol or thiol following the method described in Example 8 for the preparation of bis(5-chloro-2-hydroxy-3-nitrophenyl)-methyl isobutyl ether. Tetrahydrofuran was used as a solvent for the nucleophilic displacement reaction when required and triethylamine (1 equivalent) was found to be satisfactory as an alternative base to sodium hydride.

TABLE 2

$$O_2N\text{-}C_6H_3(Cl)(OH)\text{-}CH(R^1)\text{-}C_6H_3(Cl)(OH)\text{-}NO_2$$

| COMPOUND NO | SUBSTITUENT $R^1$ | PHYSICAL DATA m.p. °C. |
|---|---|---|
| 25 | $CH_3O$ | 149 |
| 26 | $C_2H_5O$ | 142 |
| 27 | $(CH_3)_2CHO$ | 150 |
| 28 | $CH_3OC_2H_4O$ | 110 |
| 29 | $C_6H_5CH_2O$ | 120 |
| 30 | $(CH_3)_2CHS$ | 118 |
| 31 | $(CH_3)_2CHCH_2S$ | 106 |
| 32 | $C_6H_5O$ | 202 |
| 33 | $4\text{-}CN\text{-}C_6H_4O$ | 168 |
| 34 | $3\text{-}F\text{-}C_6H_4O$ | 212 |
| 35 | $4\text{-}F\text{-}C_6H_4O$ | 139–40 |
| 36 | $C_6H_5(CH_3)CHO$ | 128–130 |
| 37 | $3\text{-}F\text{-}C_6H_4CH_2O$ | 123 |
| 38 | $4\text{-}Cl\text{-}C_6H_4CH_2O$ | 128 |
| 39 | $3\text{-}NO_2\text{-}C_6H_4CH_2O$ | 170 |
| 40 | $4\text{-}F\text{-}C_6H_4CH_2O$ | 154–155 |
| 41 | $3,5\text{-}Cl_2\text{-}C_6H_3CH_2O$ | 148 |
| 42 | $(C_6H_5)_2CHCH_2CH_2O$ | 52–55 |
| 43 | $4\text{-}Cl\text{-}2\text{-}CH_3O\text{-}C_6H_3CH_2O$ | 160–161 |
| 44 | $4\text{-}(CH_3CONH)C_6H_4O$ | 158 |
| 45 | $CH_3CH_2CH_2S$ | 118 |
| 46 | $(CH_3)_3CS$ | 150 |
| 47 | $C_2H_5(CH_3)CHS$ | 82 |
| 48 | $4\text{-}CH_3OC_6H_4CH_2S$ | 131–132 |
| 49 | $4\text{-}ClC_6H_4CH_2S$ | 110–112 |
| 50 | $C_6H_5S$ | 155–156 |
| 51 | $4\text{-}ClC_6H_4S$ | 218–220 |
| 52 | $4\text{-}NO_2C_6H_4S$ | 154–156 |

EXAMPLE 10

Compositions suitable for use as experimental injectable solutions were prepared by formulating the compounds as solutions of their salts either in water or in a mixture of water and ethylene glycol or water and polyethylene glycol (PEG200).

EXAMPLE 11

Compositions prepared by the method of Example 10 were used as a single dose to test sheep infected with sheep liver fluke (*Fasciola hepatica*). The number of liver fluke eggs in the faeces was measured at the time of treatment and at selected intervals up to 30 days after treatment. The sheep were killed and the number of adult fluke in the liver counted. The amount and structure of the active ingredient in each composition and the results of treatment of a sheep with that composition are given in the Table 3 below. The compositions were administered by sub-cutaneous injection (s/c).

TABLE 3

FLUKICIDAL ACTIVITY OF COMPOSITIONS COMPRISING AS ACTIVE INGREDIENT A COMPOUND OF GENERAL FORMULA I

| COMPOUND NO | DOSE RATE mg/kg | FAECAL EGG COUNT Eggs/g faeces (day) | POST MORTEM RESULT No. of adult fluke |
|---|---|---|---|
| 1 | 12.5 | 280(0), 0(7), 50(14), 0(30) | 0 |
| 3 | 12.5 | 110(0), 0(7), 0(14) | 1 |
| 7 | 20.0 | 360(0), 0(7), 0(13) | 0 |
| 7 | 12.5 | 240(0), 20(7), 0(14) | 0 |
| 7 | 8.0 | 120(0), 0(7), 0(14) | 0 |
| 7 | 5.0 | 400(0), 0(7), 50(14) | — |
| 8 | 12.5 | 200(0), 0(7), 0(14) | 0 |
| 8 | 8.0 | 100(0), 0(7), 0(14) | 0 |
| 8 | 6.0 | >20,000(0), 20(7), 10(14) | 0 |
| 8 | 4.0 | 150(0), 110(7), 80(14) | — |
| 9 | 12.5 | 640(0), 0(7), 0(14) | 0 |
| 10 | 12.5 | 700(0), 10(7), 90(14) | — |
| 19 | 12.5 | 400(0), 210(7), 180(14) | — |
| 20 | 12.5 | 1360(0), 400(7), 140(14) | — |
| 11 | 5.0 | 500(0), 50(7), 0(14) | 0 |
| 14[a] | 12.5 | 210(0), 0(7), 0(14) | 0 |
| 14 | 2.0 | 180(0), 60(7), 0(14) | 0 |
| 14 | 0.5 | 90(0), 0(7), 0(14) | 0 |
| 15[b] | 12.5 | 270(0), 0(7), 0(14) | 0 |
| 15 | 2.0 | 180(0), 0(7), 0(14) | 0 |
| 16 | 12.5 | 220(0), 10(7), 10(14) | 0 |
| 17 | 12.0 | 370(0), 110(7), 0(14) | 0 |
| 18 | 12.0 | 140(0), 60(7), 0(14) | 1 |
| 24 | 6.0 | 200(0), 20(7), 10(14) | 0 |
| 26 | 6.0 | 700(0), 130(7), 10(14) | 0 |
| 29 | 6.0 | 190(0), 310(7), 0(14) | 0 |
| 30 | 12.0 | 550(0), 10(7), 0(14) | 1 |
| 37 | 6.0 | 170(0), 0(7), 0(14) | 2 |
| 40 | 6.0 | 130(0), 0(7), 0(14) | 0 |
| 40 | 2.0 | 150(0), 0(7), 130(14) | — |
| 45 | 12.0 | 550(0), 10(7), 0(14) | 1 |
| 47 | 12.0 | 280(0), 10(7), 30(14) | — |
| 50 | 12.0 | 220(0), 100(7), 0(14) | 0 |
| 51 | 12.0 | 220(0), 10(7), 0(14) | 0 |
| 53[c] | 6.0 | 100(0), 0(7), 0(14) | 0 |
| 53 | 3.0 | 300(0), 460(7), 0(14) | 0 |
| 54[d] | 6.0 | 320(0), 0(7), 0(14) | 0 |
| 54 | 2.0 | 300(0), 10(7), 0(14) | 0 |
| 55 | 6.0 | 170(0), 50(7), 20(14) | 0 |
| 55 | 2.0 | 300(0), 20(7), 0(14) | 1 |

TABLE 3-continued
FLUKICIDAL ACTIVITY OF COMPOSITIONS
COMPRISING AS ACTIVE INGREDIENT
A COMPOUND OF GENERAL FORMULA I

| COMPOUND NO | DOSE RATE mg/kg | FAECAL EGG COUNT Eggs/g faeces (day) | POST MORTEM RESULT No. of adult fluke |
|---|---|---|---|
| 56 | 6.0 | 370(0), 10(7), 0(14) | 0 |

$^a$90.6% effective against immature fluke at 10 mg/kg
100% effective against immature fluke at 15 mg/kg
$^b$91.4% effective against immature fluke at 10 mg/kg
94% effective against immature fluke at 15 mg/kg
$^c$97% effective against immature fluke at 15 mg/kg
$^d$83% effective against immature fluke at 15 mg/kg

EXAMPLE 12

The minimum effective concentration of compounds of formula I against live *Fasciola hepatica* was tested by the direct application of the test compound, in solution, to live *Fasciola hepatica* in Hedon-Fleig medium. The results are given in Table 4 where the minimum effective concentration (minimum concentration required to kill *Fasciola hepatica*) was assessed 24 hours after treatment with the test compound.

TABLE 4

| COMPOUND NO | MINIMUM EFFECTIVE CONCENTRATION (parts per million) |
|---|---|
| 32 | 5 |
| 33 | 5 |
| 34 | 5 |
| 35 | 5 |
| 36 | 1 |
| 38 | 1 |
| 39 | 0.5 |
| 41 | 10 |
| 42 | 1 |
| 43 | 5 |
| 44 | 5 |
| 46 | 0.5 |
| 48 | 1 |
| 49 | 1.5 |
| 52 | 1 |
| 57 | 5 |
| 56 | 1 |

We claim:

1. A process for killing internal helminths of warm-blooded animals which process comprises treating the infected animal with an effected amount of a composition comprising as active ingredient a compound of formula I

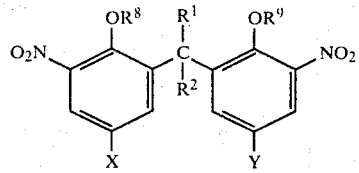

wherein $R^1$ and $R^2$ are independently chosen from the group consisting of hydrogen, $C_1$ to $C_6$ haloalkyl, $C_1$ to $C_6$ alkoxy, $C_1$ to $C_6$ alkoxyalkoxy, $C_1$ to $C_6$ alkylthio; aryloxy, arylthio, arylalkoxy and arylalkylthio wherein each aryl is phenyl substituted with one or more substituents selected from the group consisting of hydrogen, halogen, alkoxy, cyano and nitro provided that $R^1$ and $R^2$ are not both hydrogen; or $R^1$ and $R^2$ together form the group $=CR^6R^7$ wherein $R^6$ and $R^7$ are the same or different halogen; X and Y are the same or different halogen; and $R^8$ and $R^9$ are independently chosen from the group consisting of hydrogen, $C_1$ to $C_6$ alkanoyl, $C_1$ to $C_6$ alkoxycarbonyl and the cation of an inorganic or organic base.

2. A process according to claim 1 wherein $R^2$ is hydrogen and $R^8$ and $R^9$ are independently from hydrogen and the cation of an inorganic or organic base.

3. A process according to claim 1 wherein $R^1$ is $C_1$ to $C_6$ haloalkyl and $R^2$ is hydrogen or $R^1$ and $R^2$ together form the group $=CCl_2$, and $R^8$ and $R^9$ are independently chosen from hydrogen and the cation of an inorganic or organic base.

4. A process according to claim 3 wherein the haloalkyl is chosen from the group consisting of trichloromethyl, trifluoromethyl, pentafluoroethyl and heptofluoro-n-propyl.

5. A process according to claim 1 wherein at least one of $R^1$ and $R^2$ is $C_1$ to $C_6$ haloalkyl, $C_1$ to $C_6$ alkoxy and $C_1$ to $C_6$ alkylthio.

6. A process according to claim 3 wherein the compound of formula I is selected from the group consisting of 1,1-bis(5-chloro-2-hydroxy-3-nitrophenyl)-2,2,2-trichloroethane, 1,1-bis(5-chloro-2-hydroxy-3-nitrophenyl)-2,2-dichloroethylene, 1,1-bis(5-bromo-2-hydroxy-3-nitrophenyl)-2,2,2-trichloroethane, 1,1-bis(5-bromo-2-hydroxy-3-nitrophenyl)-2,2-dichloroethylene, 1,1-bis(5-chloro-2-hydroxy-3-nitrophenyl)-2,2,2-trifluoroethane and 1,1-bis(5-bromo-2-hydroxy-3-nitrophenyl)-2,2,2-trifluoroethane.

7. A process according to claim 1 wherein the internal helminth is a trematode of the Fasciola sp. or a nematode of the Haemonchus sp.

8. A process according to claim 1 wherein the internal helminth is the liver fluke (*Fasciola hepatica*).

9. A process according to claim 1 wherein the composition comprises from 1 to 20 mg of active ingredient per kilogram of animal body weight.

10. A process according to claim 1 wherein the composition, in the form of a sterile injectable composition, is administered by injection.

11. A process according to claim 1 wherein the composition, in liquid form, is administered by topical application.

12. A process according to claim 1 wherein the composition is administered by oral drench.

* * * * *